United States Patent
Agnew

(10) Patent No.: US 9,450,260 B2
(45) Date of Patent: Sep. 20, 2016

(54) METHOD FOR INFERRING TEMPERATURE IN AN ENCLOSED VOLUME

(75) Inventor: Gerard D. Agnew, Derby (GB)

(73) Assignee: LG FUEL CELL SYSTEMS INC., North Canton, OH (US)

( * ) Notice: Subject to any disclaimer, the term of this patent is extended or adjusted under 35 U.S.C. 154(b) by 718 days.

(21) Appl. No.: 13/057,827

(22) PCT Filed: Jul. 10, 2009

(86) PCT No.: PCT/EP2009/005010
§ 371 (c)(1),
(2), (4) Date: Feb. 7, 2011

(87) PCT Pub. No.: WO2010/020306
PCT Pub. Date: Feb. 25, 2010

(65) Prior Publication Data
US 2011/0129934 A1 Jun. 2, 2011

(30) Foreign Application Priority Data
Aug. 19, 2008 (GB) .................................. 0815017.9

(51) Int. Cl.
*G01N 33/20* (2006.01)
*G01R 27/08* (2006.01)
(Continued)

(52) U.S. Cl.
CPC .......... *H01M 8/04656* (2013.01); *G01K 3/005* (2013.01); *G01K 7/183* (2013.01); *G01N 31/22* (2013.01); *G01N 33/84* (2013.01);
(Continued)

(58) Field of Classification Search
CPC .............................. G01N 31/22; G01N 33/84
USPC .................... 436/151, 149, 160; 347/37, 36; 340/521, 577, 581, 628
See application file for complete search history.

(56) References Cited

U.S. PATENT DOCUMENTS

| 1,583,600 A | 8/1922 | McBurney |
| 3,593,563 A | 7/1971 | Marmor et al. |

(Continued)

FOREIGN PATENT DOCUMENTS

| CN | 200941319 Y | 8/2007 |
| DE | 552706 C | 6/1932 |

(Continued)

OTHER PUBLICATIONS

British Search Report dated Oct. 13, 2008 issued in British Patent Application No. 0815017.9.

(Continued)

*Primary Examiner* — Krishnan S Menon
*Assistant Examiner* — Dwan A Gerido
(74) *Attorney, Agent, or Firm* — Oliff PLC

(57) ABSTRACT

A method for inferring temperature in an enclosed volume containing a fuel/oxidant mixture, the method comprises placing at least one wire in the enclosed volume. The at least one wire having an identifiable property wherein the identifiable property of the at least one wire changes from a first identifiable state at a temperature below the auto-ignition temperature of the fuel/oxidant mixture to a second identifiable state at a temperature above the auto-ignition temperature of the fuel/oxidant mixture, and determining if the identifiable property of the at least one wire has changed from the first identifiable state to the second identifiable state and hence if the temperature in the enclosed volume is above the auto-ignition temperature of the fuel/oxidant mixture.

18 Claims, 4 Drawing Sheets

(51) Int. Cl.
  *H01M 8/04* (2016.01)
  *G01K 3/00* (2006.01)
  *G01K 7/18* (2006.01)
  *G01N 31/22* (2006.01)
  *G01N 33/84* (2006.01)
  *H01M 8/12* (2016.01)

(52) U.S. Cl.
  CPC ........ *H01M 8/0432* (2013.01); *H01M 8/0444* (2013.01); *H01M 2008/1293* (2013.01); *Y02E 60/50* (2013.01); *Y02E 60/525* (2013.01)

(56) References Cited

U.S. PATENT DOCUMENTS

| | | | | |
|---|---|---|---|---|
| 2003/0112140 | A1* | 6/2003 | Everson et al. | 340/521 |
| 2007/0243434 | A1 | 10/2007 | Jahnke et al. | |
| 2008/0226505 | A1* | 9/2008 | Willettt et al. | 422/98 |
| 2009/0258267 | A1* | 10/2009 | Mergler et al. | 429/22 |

FOREIGN PATENT DOCUMENTS

| | | |
|---|---|---|
| DE | 37 30 046 A1 | 3/1989 |
| GB | 721077 A | 12/1954 |
| JP | A-8-260077 | 10/1996 |
| JP | A-2005-233487 | 9/2005 |
| WO | WO 98/18002 A1 | 4/1998 |
| WO | WO 03/048692 A1 | 6/2003 |
| WO | WO 2006/106288 A3 | 10/2006 |

OTHER PUBLICATIONS

International Search Report mailed Oct. 5, 2009 issued in International Patent Application No. PCT/EP2009/005010.

Written Opinion of the International Searching Authority mailed Oct. 5, 2009 issued in International Patent Application No. PCT/EP2009/005010.

Dec. 17, 2015 Office Action issued in Canadian Application No. 2,733,351.

* cited by examiner

METHOD FOR INFERRING TEMPERATURE IN AN ENCLOSED VOLUME

The present invention relates to a method for inferring temperature in an enclosed volume and in particular to a method for inferring temperature in an enclosed volume disposed within a fuel cell.

It is known that a fuel cell arrangement comprises one or more fuel cell modules, each fuel cell module comprises a plurality of fuel cells arranged within a housing and the housing of each fuel cell module is arranged within a pressure vessel. Conventionally the pressure vessel has internal insulation and/or cooling fluid using passages within the pressure vessel to maintain the temperature of the pressure vessel at a sufficiently low temperature to guarantee the integrity of the pressure vessel. In the case of solid oxide fuel cells operating at higher temperatures, for example 700° C. to 1,000° C., the thermal management of the heat flux to the pressure vessel is difficult. Thermocouple devices are typically employed to monitor such elevated temperatures. However, thermocouple devices are known to have low signal output and to be significantly non-linear in their response. The signal is also vulnerable to electrical noise in practical applications, leading to unreliability issues due to junction degradation. Furthermore, high temperature thermocouple devices are costly.

Accordingly the present invention seeks to provide a novel method for inferring temperature in an enclosed volume, which reduces, preferably overcomes, the above mentioned problem.

Accordingly the present invention provides a method for inferring temperature in an enclosed volume, the enclosed volume containing a fuel/oxidant mixture or being supplied with a fuel and an oxidant to form a fuel/oxidant mixture in the enclosed volume, the method comprising placing at least one wire in the enclosed volume, the at least one wire having an identifiable property wherein the identifiable property of the at least one wire changes from a first identifiable state at a temperature below the auto-ignition temperature of the fuel/oxidant mixture to a second identifiable state at a temperature above the auto-ignition temperature of the fuel/oxidant mixture, and determining if the identifiable property of the at least one wire has changed from the first identifiable state to the second identifiable state and hence if the temperature in the enclosed volume is above the auto-ignition temperature of the fuel/oxidant mixture.

Preferably the method further comprises indicating that the identifiable property of the at least one wire has changed from the first identifiable state to the second identifiable state and hence the temperature in the enclosed volume is above the auto-ignition temperature of the fuel/oxidant mixture.

The enclosed volume may be a volume encased by the at least one wire.

The enclosed volume may be a volume between an outer volume and an inner volume, the outer volume encasing the inner volume.

Preferably the identifiable property of the at least one wire is electrical resistance.

Preferably the first identifiable state is electrical resistance and the second identifiable state is electrical conductance.

Alternatively the identifiable property of the at least one wire is electrochemical state.

Alternatively the first identifiable state is an oxidised state and the second identifiable state is a reduced state.

Preferably the at least one wire is selected from the group consisting of Pt, Pd, Rh, Ru and alloys thereof.

More preferably the at least one wire is substantially Pd.

Preferably a plurality of spokes are arranged on the at least one wire.

More preferably the plurality of spokes are thermally conducting.

More preferably the plurality of spokes are selected from the group consisting of Cu, Ni, W, Ag, alloys thereof and diamond coating.

The enclosed volume may be disposed within a fuel cell.

The enclosed volume may be disposed within a solid oxide fuel cell.

The enclosed volume may be disposed within a reformer.

The enclosed volume may be disposed within a hydrocarbon reformer.

The present invention will be more fully described by way of example with reference to the accompanying drawings in which:—

Figure 1:
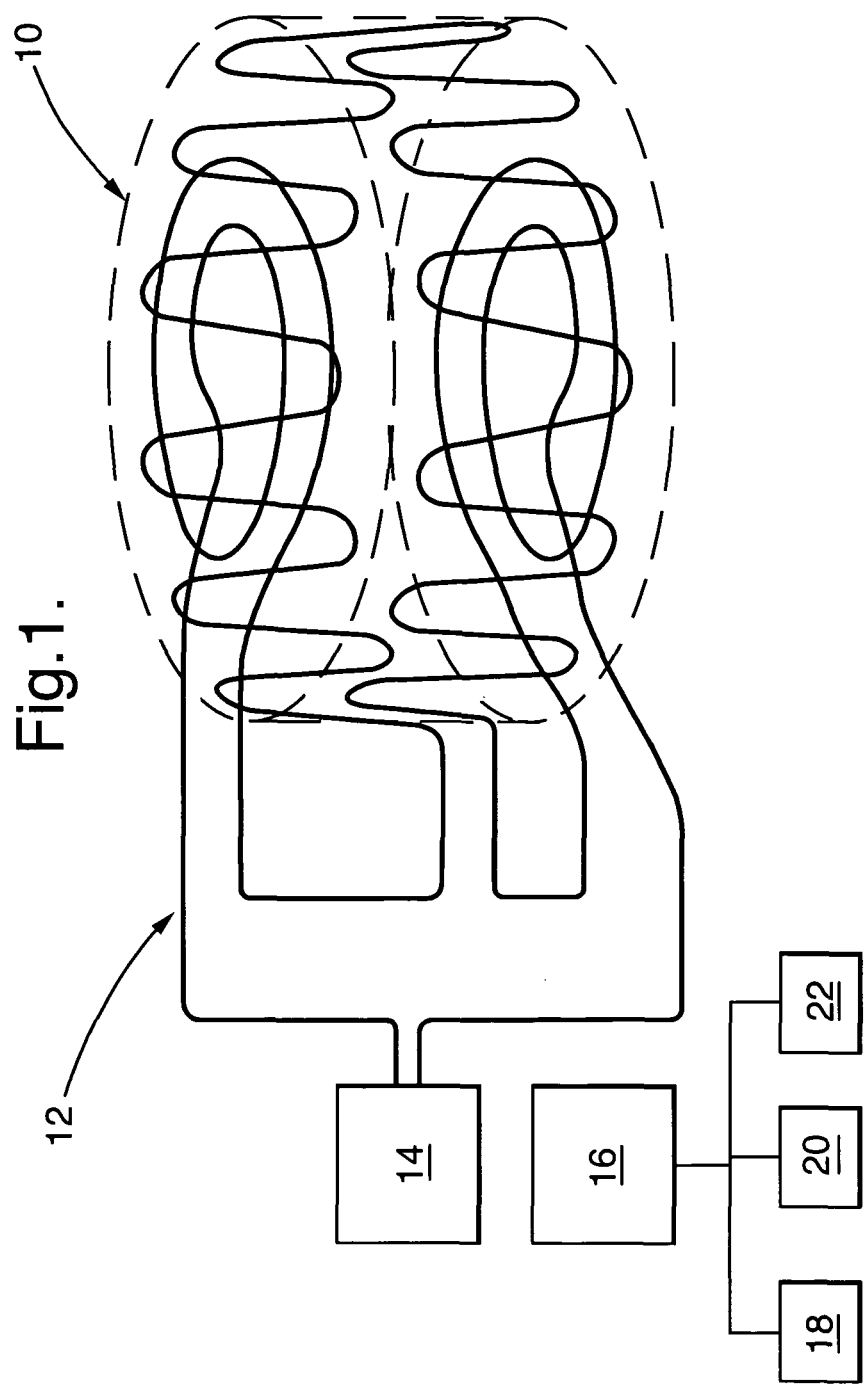
FIG. 1 shows a perspective view of a first embodiment according to the present invention.

A method for inferring temperature in an enclosed volume 10 according to a first embodiment of the present invention is shown in FIG. 1. At least one wire 12 is placed in the enclosed volume 10 by forming the at least one wire into a shape encasing the enclosed volume 10 whose temperature is to be inferred. In particular, the at least one wire 12 is arranged to extend around the periphery of the enclosed volume 10 while remaining in the enclosed volume 10. The at least one wire 12, for example, extends circumferentially and axially in a cylindrical casing to form a sinusoidally shaped wire. Thus, the at least one wire 12 is positioned within a thin region on the inside of the surface of the casing defining the enclosed volume 10. The enclosed volume 10 initially contains a fuel/oxidant mixture having an auto-ignition temperature. The at least one wire 12 has an identifiable property whereby the identifiable property changes from a first identifiable state at a temperature below the auto-ignition temperature of the fuel/oxidant mixture to a second identifiable state at a temperature above the auto-ignition temperature of the fuel/oxidant mixture. The identifiable property of the at least one wire 12 is then determined by a determining device 14 connected to the at least one wire 12 to see if the identifiable property has changed from the first identifiable state to the second identifiable state and hence if the temperature in the enclosed volume is above the auto-ignition temperature of the fuel/oxidant mixture. A control device 16 is provided to indicate that the identifiable property of the at least one wire 12 has changed from the first identifiable state to the second identifiable state and hence the temperature in the enclosed volume is above the auto-ignition temperature of the fuel/oxidant mixture. The control device 16 operates an alarm system, for example an audible alarm 18 and/or visual alarm 20. The control device 16 may also operate a pump 22 whereby the fuel/oxidant mixture is pumped out of the enclosed volume to prevent explosion and/or water or other extinguishing fluids are flushed into the enclosed volume to put out the fire.

Alternatively, a fuel and an oxidant may be supplied to the enclosed volume 10 to form a fuel/oxidant mixture in the enclosed volume 10.

The at least one wire 12 may be a thin continuous wire or made up of a series of wires connected continuously and wired electrically in series.

In one embodiment, the identifiable property of the at least one wire is electrical resistance, the first identifiable state of the at least one wire is electrical resistance and the second identifiable state is electrical conductance. Accordingly, the electrical resistance of the at least one wire 12, for example a platinum (Pt) wire, changes from being electrically resistant at temperatures below the auto-ignition temperature of the fuel/oxidant mixture to being electrically conducting at temperatures above the auto-ignition temperature of the fuel/oxidant mixture. The change in the electrical resistance may be monitored and determined by the determining device 14, for example, resistance measurement devices known in the art.

In another embodiment, the identifiable property of the at least one wire 12 is electrochemical state, the first identifiable state of the at least one wire 12 is an oxidised state and the second identifiable state is a reduced state. Accordingly, the electrochemical state of the at least one wire 12, for example a palladium (Pd) wire, changes from an oxidised state at temperatures below the auto-ignition temperature of the fuel/oxidant mixture to a reduced state at temperatures above the auto-ignition temperature of the fuel/oxidant mixture. The change in the electrochemical state may be monitored and determined by the determining device 14, for example, a change in colour of the at least one wire 12.

The at least one wire 12 is selected from the group consisting of platinum (Pt), palladium (Pd), rhodium (Rh), ruthenium (Ru), and alloys thereof. A threshold temperature of a given fuel/oxidant mixture is herein defined to be a predetermined temperature above the auto-ignition temperature of the fuel/oxidant mixture in the enclosed volume 10. A transition temperature of the at least one wire 12 is herein defined as the temperature close to or at which the identifiable property changes from the first identifiable state to the second identifiable state. For a solid oxide fuel cell system supplied with a natural gas and an air mixture, the threshold temperature of the solid oxide fuel cell system needs to be maintained above approximately 800° C. In this case, the at least one wire 12 is preferably substantially Pd. Although the transition temperature of the at least one wire 12 varies a little with the oxygen partial pressure in the solid oxide fuel cell system, alloying of the Pd wire with a small quantity of gold (Au) or Pt could be used to achieve the appropriate threshold temperature. Knowledge of the auto-ignition temperature of the fuel/oxidant mixture and the transition temperature of the at least one wire 12 ensures the right composition of the at least one wire 12 is used, in other words the at least one wire 12 is composition-tunable. Further, by enclosing the volume 10 in the at least one wire 12, any localised lowering of any portion of the at least one wire 12 below the threshold temperature results in a sharp change in the identifiable state of the at least one wire 12 even if the remaining portion of the at least one wire 12 is above the threshold temperature.

Figure 2:
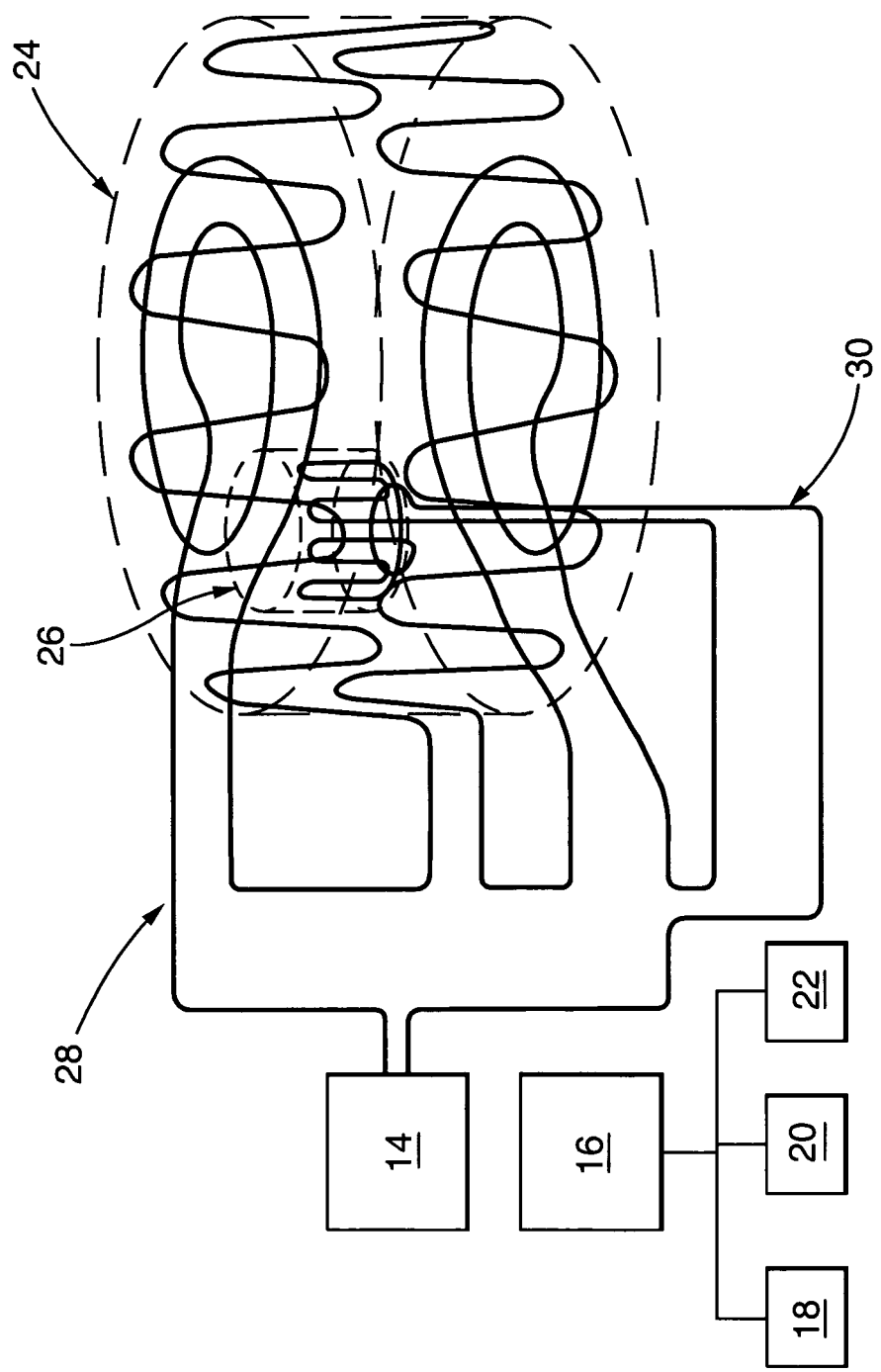
FIG. 2 shows a perspective view of a second embodiment according to the present invention.

FIG. 2 shows another embodiment of the present invention and like parts are denoted by like numerals. The embodiment illustrated in FIG. 2 differs from that of FIG. 1 in that an outer volume 24 encases an inner volume 26. The outer volume 24 is provided with at least one first wire 28. The inner volume 26 is provided with at least one second wire 30 in a similar fashion. In this case, the temperature of the enclosed volume 10 to be inferred is the temperature of the volume between the outer volume 24 and the inner volume 26. The at least one first wire 28 and the at least one second wire 30 may be formed by one continuous wire or separate wires electrically connected in series. The inner volume 26 may be regions containing sources of heat sinks or cooling, such as endothermic reforming components.

Figure 3:
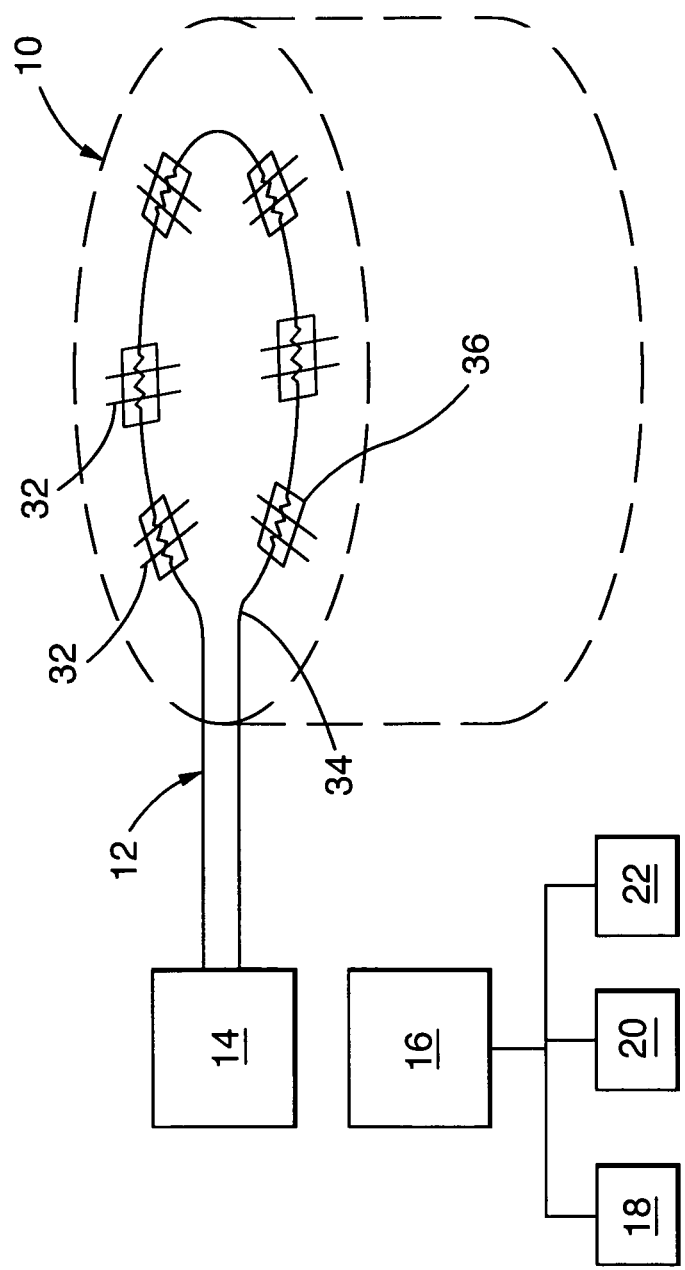
FIG. 3 shows a perspective view of a third embodiment according to the present invention.

A further embodiment of the present invention is shown in FIG. 3 and like parts are denoted by like numerals. The embodiment illustrated in FIG. 3 differs from that of FIG. 1 in that a plurality of spokes 32 are arranged on the at least one wire 12 in a mesh arrangement. The plurality of spokes 32 may be thermally conducting. The plurality of spokes 32 are selected from the group consisting of copper (Cu), nickel (Ni), tungsten (W), silver (Ag), alloys thereof and diamond coating, a wire having a diamond coating. By having the plurality of spokes 32 on the at least one wire 12, the area coverage for thermal monitoring and detection of localised lowering of temperature below the threshold temperature is increased. Another advantage of providing a plurality of thermally conducting spokes 32 is that the amount of precious metals or alloys used for the at least one wire 12 is reduced compared to using the at least one wire 12 alone. By thinning the at least one wire 12 and flattening its cross-sectional geometry, the proportion of the cross-section close to the surface of the at least one wire 12 may be increased and the rate of response could be improved, thereby further reducing the material used for the at least one wire 12. Further improvement in sensitivity and rate of response could be achieved, for example, by monitoring the conductivity of the at least one wire 12 with high frequency AC signals that are more confined to the surface layer of the at least one wire 12.

Turning again to FIG. 3, the at least one wire 12 may be replaced by a layer of sintered porous conductor 34 deposited on an electrically insulating substrate by conventional thick film or thin film methods in order to further increase sensitivity. The top of the enclosed volume 10 is covered with the plurality of spokes 32 and discrete thick film components 36 whereby the thick film components 36 are electrically connected in series. By using a plurality of discrete thick film components 36 in conjunction with a plurality of spokes 32, a large surface coverage and hence increased sensitivity could be achieved.

Figure 4:
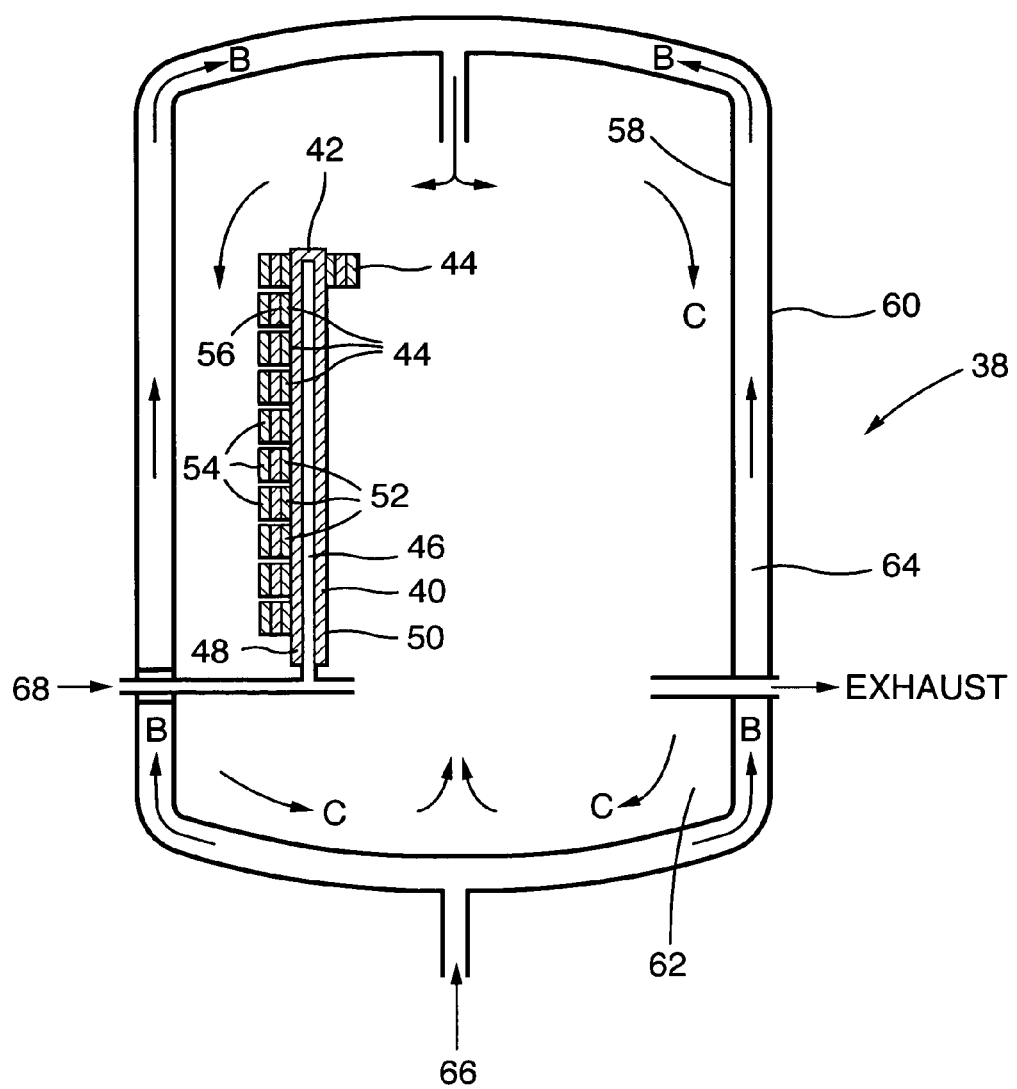
FIG. 4 illustrates the use of the present invention in a fuel cell arrangement.

The present invention may be used within a fuel cell arrangement described in PCT Publication No. WO 2006/106288A2, the entire content of which is incorporated herein for reference. In FIG. 4, the fuel cell arrangement 38 comprises at least one solid oxide fuel cell module 40, preferably there are a plurality of solid oxide fuel cell modules 40. Each solid oxide fuel cell module 40 comprises a hollow porous support member 42 and a plurality of solid oxide fuel cells 44. Each hollow porous support member 42 has at least one chamber 46 extending therethrough and comprises two planar, parallel, flat surfaces 48 and 50 upon which the solid oxide fuel cells 44 are arranged. Each solid oxide fuel cell module 40 is a sealed assembly, while allowing the flow of fuel through the at least one chamber 46 in the hollow porous support member 42. Each solid oxide fuel cell 44 comprises an anode electrode 52, a cathode electrode 54 and an electrolyte 56. The solid oxide fuel cells 44 are arranged such that the anode electrodes 52 are arranged on the outer surface, the two planar, parallel, flat surfaces 48 and 50, of the hollow porous support member 42, the electrolytes 56 are arranged on the anode electrodes 52 and the cathode electrodes 54 are arranged on the electrolytes 60. The solid oxide fuel cells 44 are also arranged such that the anode electrode 52 of one solid oxide fuel cell 44 is electrically connected in series with the cathode electrode of an adjacent solid oxide fuel cell 44. In this arrangement each solid oxide fuel cell module 40 is arranged within a single inner vessel 58, and the inner vessel 58 is arranged within an outer pressure vessel 60. In this arrangement the inner vessel 58 defines a space 62 and a space 64 is defined between the inner vessel 58 and the outer pressure vessel 60. There are means 66 to supply oxidant to the cathode electrodes 54 of the solid oxide fuel cells 44 of the at least one fuel cell module 40 and there are means 68 to supply fuel to the anode electrodes of the solid oxide fuel cells 44 of the at least one solid oxide fuel cell module 40. As the operating temperature of the solid oxide fuel cells easily reaches the range of about 700° C. to 1,000° C., extra care must be taken to ensure that the supplied fuel and oxidant do not mix, which would otherwise lead to an explosion at such high operating temperature. Mixing of the fuel and oxidant may result, for example, from a rupture of the at least one chamber 46 or a leak in the anode electrode 52, cathode electrode 54 or electrolyte 56. By placing at least one wire 12 in the enclosed volume 10 in the inner vessel 58 as taught in the present invention, confirmation could be obtained that enclosed volume 10 in the inner vessel 58 is above the threshold temperature within a high degree of accuracy.

The present invention enables the selection of a physical and electrical configuration of at least one wire 12 to reliably infer that an enclosed volume 10 is either above the auto-ignition temperature or that no more than a certain fraction is at or below the auto-ignition temperature of a fuel/oxidant mixture. By choosing the path of the at least one wire 12 so that it lies in a thin region on the inside of a surface that encloses the volume 10 to be monitored and choosing the transition temperature of the at least one wire 12 with knowledge of the heat transfer regime in the enclosed volume 10, confirmation could be obtained that the enclosed volume 10 is above the threshold temperature within a high degree of accuracy.

The at least one wire may have two identifiable properties and both identifiable properties change from a first identifiable state at a temperature below the auto-ignition temperature of the fuel/oxidant mixture to a second identifiable state at a temperature above the auto-ignition temperature of the fuel/oxidant mixture. As mentioned previously the at least one wire changes from an oxidised state at temperatures below the auto-ignition temperature of the fuel/oxidant mixture to a reduced state of temperatures about the auto-ignition temperature of the fuel/oxidant mixture. In addition to the change of electrochemical state of the at least one wire the at least one wire also changes from being electrically resistant at temperatures below the auto-ignition temperature of the fuel/oxidant mixture because it is in an oxidised state to being electrically conducting at temperatures above the auto-ignition temperature of the fuel/oxidant mixture because it is a reduced state.

Advantages of the present invention include the elimination of costly high temperature thermocouples which are unreliable due to junction degradation. A single electrical subsystem could be employed for a large volume to be monitored where previously electrical subsystems were required for every thermocouple placed in the volume. The state of an enclosed volume 10 above the auto-ignition temperature may be monitored with much less instrumentation than before. In place of thermocouples, simpler electronics may be used, allowing higher levels of safety to be achieved with less analysis and testing/evaluation.

The present invention is applicable to devices operating at high temperatures involving explosive fluids, and in particular to fuel cells such as solid oxide fuel cells and reformers such as hydrocarbon reformers.

The invention claimed is:

1. A method for inferring temperature in an enclosed volume, the enclosed volume either containing a fuel/oxidant mixture with a predetermined auto-ignition temperature or being supplied with a fuel and an oxidant to form a fuel/oxidant mixture with the predetermined auto-ignition temperature in the enclosed volume, the method comprising:
   (i) placing at least one wire in the enclosed volume, the at least one wire having a transition temperature at which an identifiable property of the at least one wire changes from a first identifiable state to a second identifiable state, wherein
      the materials of the at least one wire are selected such that the transition temperature of the at least one wire is at or above the predetermined auto-ignition temperature of the fuel/oxidant mixture,
      the first identifiable state is observed at a temperature below the predetermined auto-ignition temperature of the fuel/oxidant mixture, and
      second identifiable state is observed at a temperature at or above the predetermined auto-ignition temperature of the fuel/oxidant mixture; and
   (ii) determining if the identifiable property of the at least one wire has changed from the first identifiable state to the second identifiable state and hence if the temperature in the enclosed volume is at or above the predetermined auto-ignition temperature of the fuel/oxidant mixture,
   wherein:
   the identifiable property of the at least one wire is a change in electrochemical state,
   the first identifiable state is an oxidized state and the second identifiable state is a reduced state in which (i) the change in electrochemical state of the at least one wire from the first identifiable state to the second identifiable state involves determining a color change of the at least one wire in which the color change is determined by a determining device or (ii) the change in electrochemical state of the at least one wire from the first identifiable state to the second identifiable state involves determining a change in resistivity in the at least one wire in which the wire changes from being electrically resistive in the first identifiable state to being more electrically conductive in the second identifiable state.

2. A method according to claim 1 wherein the method further comprises indicating that the identifiable property of the at least one wire has changed from the first identifiable state to the second identifiable state and hence the temperature in the enclosed volume is above the predetermined auto-ignition temperature of the fuel/oxidant mixture.

3. A method according to claim 1 wherein the enclosed volume is a volume encased by the at least one wire.

4. A method according to claim 1 wherein the enclosed volume is a volume between an outer volume and an inner volume, the outer volume encasing the inner volume.

5. A method according to claim 1 wherein the transition temperature of the at least one wire is the same as the predetermined auto-ignition temperature of the fuel/oxidant mixture.

6. The method according to claim 1 wherein the at least one wire is in direct contact with the fuel/oxidant mixture in the enclosed volume.

7. A method according to claim 1 wherein the enclosed volume is disposed within a fuel cell.

8. A method according to claim 7 wherein the enclosed volume is disposed within a solid oxide fuel cell.

9. A method according to claim 1 wherein the enclosed volume is disposed within a reformer.

10. A method according to claim 9 wherein the enclosed volume is disposed within a hydrocarbon reformer.

11. A method according to claim 1 wherein the at least one wire is selected from the group consisting of Pt, Pd, Rh, Ru and alloys thereof.

12. A method according to claim 11 wherein the at least one wire is substantially Pd.

13. A method according to claim 11 wherein the at least one wire reduces from a non-conducting oxide to a conducting metal at the transition temperature of the at least one wire, the transition temperature of the at least one wire being above but close to the predetermined auto-ignition temperature of the fuel/oxidant mixture.

14. A method according to claim 11, wherein the at least one wire comprises metals or alloys selected from the group consisting of Pd, Rh, Pt, and Ru, the metals or alloys being selected such that the at least one wire changes from a non-conducting oxide to a conducting metal at the transition temperature of the at least one wire, the transition temperature of the at least one wire being above but close to the predetermined auto-ignition temperature of the fuel/oxidant mixture.

15. A method according to claim 14 wherein the transition temperature of the at least one wire is the same as the predetermined auto-ignition temperature of the fuel/oxidant mixture.

16. A method according to claim 1 wherein a plurality of spokes are arranged on the at least one wire.

17. A method according to claim 16 wherein the plurality of spokes are thermally conducting.

18. A method according to claim 17 wherein the plurality of spokes are selected from the group consisting of Cu, Ni, W, Ag, alloys thereof and diamond coating.

* * * * *